(12) United States Patent
Abe

(10) Patent No.: US 10,012,617 B2
(45) Date of Patent: Jul. 3, 2018

(54) PHOTOACOUSTIC APPARATUS, OPERATION METHOD OF PHOTOACOUSTIC APPARATUS, AND PROGRAM

(71) Applicant: CANON KABUSHIKI KAISHA, Tokyo (JP)

(72) Inventor: Hiroshi Abe, Kyoto (JP)

(73) Assignee: Canon Kabushiki Kaisha, Tokyo (JP)

( * ) Notice: Subject to any disclaimer, the term of this patent is extended or adjusted under 35 U.S.C. 154(b) by 940 days.

(21) Appl. No.: 14/503,949

(22) Filed: Oct. 1, 2014

(65) Prior Publication Data

US 2015/0098305 A1 Apr. 9, 2015

(30) Foreign Application Priority Data

Oct. 4, 2013 (JP) .................................. 2013-209625

(51) Int. Cl.
*A61B 5/00* (2006.01)
*G01N 29/24* (2006.01)
*G01N 29/06* (2006.01)

(52) U.S. Cl.
CPC ....... *G01N 29/2418* (2013.01); *A61B 5/0095* (2013.01); *A61B 5/7235* (2013.01); *G01N 29/0654* (2013.01)

(58) Field of Classification Search
USPC ....................................................... 367/140
See application file for complete search history.

(56) References Cited

U.S. PATENT DOCUMENTS

2008/0194929 A1* 8/2008 Pesach ................. A61B 5/0066
600/310
2008/0252891 A1* 10/2008 Uber ................... G01N 21/1702
356/437
2009/0054763 A1* 2/2009 Wang ................... A61B 5/0059
600/425

(Continued)

OTHER PUBLICATIONS

"Photoacoustic Tomography: In Vivo Imaging From Organelles to Organs",Lihong V.Wang Song Hu,Science 335,1458 (2012)).

(Continued)

*Primary Examiner* — James R Hulka
(74) *Attorney, Agent, or Firm* — Canon USA, Inc. I.P. Division

(57) ABSTRACT

A photoacoustic apparatus disclosed in the present specification includes: an acoustic wave transmission unit configured to transmit a transmission acoustic wave to a specific area; a control unit configured to control a transmission waveform of the transmission acoustic wave transmitted from the acoustic wave transmission unit; a light source configured to generate light emitted to an area including the specific area when the acoustic wave reaches the specific area; an acoustic wave reception unit configured to receive the acoustic wave and to output a time-series received signal; and a signal processing unit configured to acquire optical property information based on the time-series received signal, wherein the control unit controls the transmission waveform in such a manner that amplitude of a photoacoustic wave generated in the specific area is reduced by the transmission acoustic wave transmitted from the acoustic wave transmission unit.

18 Claims, 6 Drawing Sheets

(56) References Cited

U.S. PATENT DOCUMENTS

| | | | | |
|---|---|---|---|---|
| 2009/0312628 | A1* | 12/2009 | Igarashi | A61B 5/0068 600/425 |
| 2010/0049044 | A1* | 2/2010 | Burcher | A61B 5/0059 600/437 |
| 2011/0230761 | A1* | 9/2011 | Peyman | A61K 41/0028 600/431 |
| 2011/0232385 | A1* | 9/2011 | Nanaumi | A61B 5/0095 73/602 |
| 2011/0245652 | A1* | 10/2011 | Oishi | A61B 5/0059 600/407 |
| 2011/0319743 | A1* | 12/2011 | Satoh | A61B 5/0095 600/407 |
| 2012/0197113 | A1* | 8/2012 | Courtney | A61B 8/12 600/427 |
| 2012/0253180 | A1* | 10/2012 | Emelianov | A61B 8/0841 600/424 |
| 2012/0259198 | A1* | 10/2012 | Nagae | A61B 5/0095 600/407 |
| 2013/0023752 | A1* | 1/2013 | Khuri-Yakub | A61B 5/0095 600/407 |
| 2013/0137960 | A1* | 5/2013 | Lisogurski | A61B 5/0095 600/407 |
| 2013/0197401 | A1* | 8/2013 | Sato | A61N 7/00 601/2 |
| 2013/0261427 | A1* | 10/2013 | Oishi | A61B 5/0095 600/407 |
| 2013/0274585 | A1* | 10/2013 | Wanda | A61B 5/0095 600/407 |
| 2013/0322204 | A1* | 12/2013 | Ebisawa | G01S 15/8965 367/7 |
| 2014/0005537 | A1* | 1/2014 | Asami | A61B 5/0095 600/431 |
| 2014/0114172 | A1* | 4/2014 | Abe | A61B 5/0095 600/407 |
| 2015/0007659 | A1* | 1/2015 | Nanaumi | A61B 5/0095 73/602 |
| 2015/0099973 | A1* | 4/2015 | Abe | G01N 21/1702 600/440 |
| 2015/0351639 | A1* | 12/2015 | Abe | A61B 8/4416 600/407 |
| 2016/0199241 | A1* | 7/2016 | Rapoport | A61G 11/00 600/22 |

OTHER PUBLICATIONS

"Acoustic radiation force impulse imaging of myocardial radio-frequency ablation: initial in vivo results", Fahey et al., IEEE Transactions on Ultrasonics, Ferroelectrics and Frequency Control, vol. 52, Issue 4, Apr. 2005 pp. 631-641.

* cited by examiner

PHOTOACOUSTIC APPARATUS, OPERATION METHOD OF PHOTOACOUSTIC APPARATUS, AND PROGRAM

BACKGROUND OF THE INVENTION

Field of the Invention

The present invention relates to a photoacoustic apparatus which acquires optical property information by using a photoacoustic wave, an operation method of the photoacoustic apparatus, and a program.

Description of the Related Art

A study of an optical imaging apparatus to image information inside a subject, which information is acquired by emitting light from a light source such as a laser to the subject such as a living body and acquired based on the incident light, has been actively done in a medical field. As one kind of the optical imaging technique, there is photoacoustic imaging (PAI). In the photoacoustic imaging, pulsed light generated in a light source is emitted to a subject and an acoustic wave (typically, ultrasonic wave) generated in a subject tissue which absorbs energy of the pulsed light propagated and diffused in the subject is received. Based on the received signal, imaging of information of the subject is reconstructed.

That is, by using a difference between absorptance of optical energy in an object region such as a tumor and that in other tissues, an elastic wave (photoacoustic wave) generated when a region to be inspected absorbs the emitted optical energy and instantaneously expands is received by a probe. By performing mathematical analysis processing on this received signal, optical property distribution inside the subject, specifically, initial sound pressure distribution, optical energy absorption density distribution, absorption coefficient distribution, or the like can be acquired.

These pieces of information can also be used, for example, for a quantitative measurement of a specific substance inside the subject such as oxygen saturation in blood. Recently, by using the photoacoustic imaging, a preclinical study to image a blood vessel image of a small animal or a clinical study to apply this principle to a diagnosis of a breast cancer or the like has been actively done ("Photoacoustic Tomography: In Vivo Imaging From Organelles to Organs", Lihong V. Wang Song Hu, Science 335, 1458 (2012)). In the photoacoustic imaging, generally, it is desired to image optical property distribution of an optical absorber inside the subject.

SUMMARY OF THE INVENTION

A photoacoustic apparatus disclosed in the present specification includes: an acoustic wave transmission unit configured to transmit a transmission acoustic wave to a specific area; a control unit configured to control a transmission waveform of the transmission acoustic wave transmitted from the acoustic wave transmission unit; a light source configured to generate light emitted to an area including the specific area when the acoustic wave reaches the specific area; an acoustic wave reception unit configured to receive the acoustic wave and to output a time-series received signal; and a signal processing unit configured to acquire optical property information based on the time-series received signal, wherein the control unit controls the transmission waveform in such a manner that amplitude of a photoacoustic wave generated in the specific area is reduced by the transmission acoustic wave transmitted from the acoustic wave transmission unit.

Further features of the present invention will become apparent from the following description of exemplary embodiments (with reference to the attached drawings).

DESCRIPTION OF THE EMBODIMENTS

Figure 1:
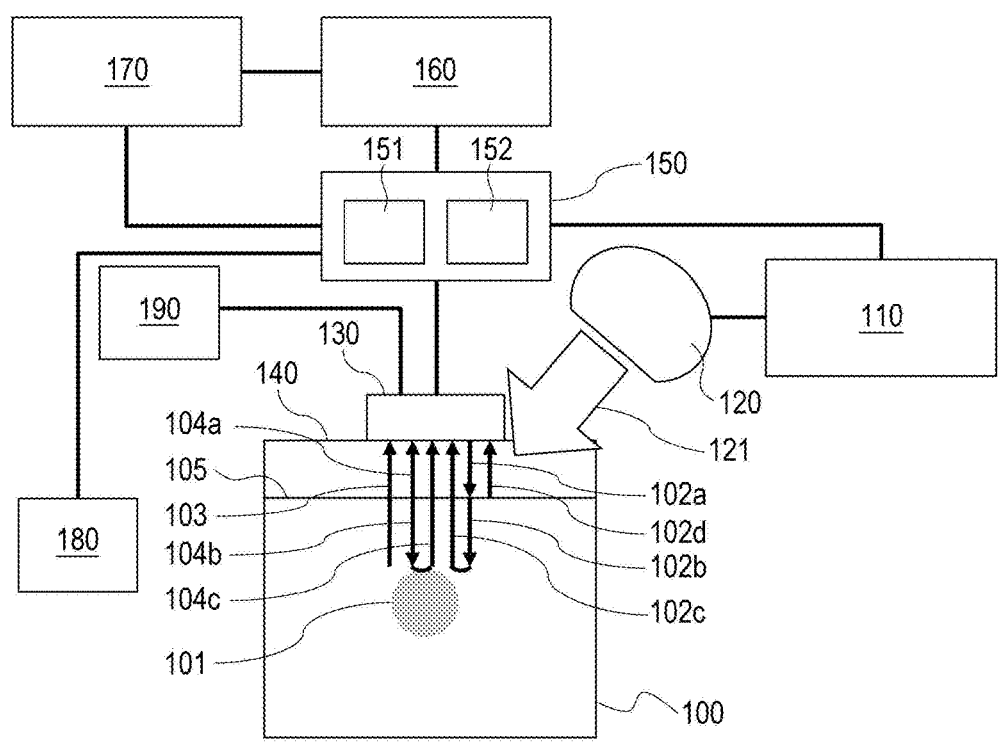
FIG. 1 is a schematic view illustrating a photoacoustic apparatus according to a first embodiment.

A photoacoustic wave generated in an optical absorber is transmitted and propagated isotropically with a shape of the optical absorber figure as an origin. Then, a probe receives not only a photoacoustic wave directly propagated thereto from the optical absorber but also a reflected wave generated due to reflection, in a subject, of the photoacoustic wave generated in the optical absorber. Since the reflected wave is not propagated to the probe directly and takes different time of flight, reconstructed image does not depict a true optical absorber. Then, decrease in quantitativity of optical property information acquired from a received signal including a component corresponding to this reflected wave is caused.

A photoacoustic apparatus disclosed in the present specification transmits a transmission acoustic wave to a specific area. Then, when the transmission acoustic wave reaches the specific area, the photoacoustic apparatus disclosed in the present specification emits light to an area including the specific area and generates a photoacoustic wave in the specific area. Accordingly, the transmission acoustic wave transmitted to the specific area and the photoacoustic wave generated in the specific area are superimposed and an interference wave is formed.

Here, the photoacoustic apparatus disclosed in the present specification controls a waveform of the transmission acoustic wave transmitted to the specific area in such a manner that amplitude of the photoacoustic wave generated in the specific area is reduced. That is, the photoacoustic apparatus disclosed in the present specification controls a transmission waveform of the transmission acoustic wave in such a manner that amplitude of the interference wave becomes smaller than amplitude of the photoacoustic wave generated in the specific area. Thus, amplitude of a reflected wave generated due to reflection of the interference wave becomes smaller than amplitude of a reflected wave generated due to reflection of the photoacoustic wave generated in the specific area.

Also, the photoacoustic apparatus disclosed in the present specification acquires optical property information from a received signal of the photoacoustic wave including the interference wave. The optical property information acquired in such a manner becomes information from which a component of a reflected wave of the photoacoustic wave generated in the specific area is reduced.

As described, according to the photoacoustic apparatus disclosed in the present specification, decrease in quantitativity of the optical property information due to a component corresponding to a reflected wave of the photoacoustic wave can be controlled.

Especially, amplitude of a photoacoustic wave generated in a part to which light is directly emitted, such as a skin on a surface of a subject or an acoustic lens arranged on a surface of a probe is large, and thus, amplitude of a reflected wave thereof also becomes large. Thus, quantitativity of the optical property information is greatly decreased due to such a reflected wave. Thus, in each embodiment, a case where a waveform of a transmission acoustic wave to be transmitted is controlled in such a manner that amplitude of a photoacoustic wave generated on a surface of a subject is reduced will be described. That is, in each embodiment, a surface of a subject to which light is emitted will be described as a source of a reflected wave.

Note that as the optical property information, there are initial sound pressure distribution of a photoacoustic wave, optical energy absorption density distribution, absorption coefficient distribution, concentration distribution of a substance included in a subject, and the like. Here, a concentration of a substance is, for example, oxygen saturation, an oxyhemoglobin concentration, a deoxyhemoglobin concentration, or a total hemoglobin concentration.

Also, a reflected wave in the present specification includes an acoustic wave generated by scattering.

In the following, embodiments of a photoacoustic apparatus according to the present invention will be described in detail with reference to the attached drawings. However, the scope of the invention is not limited to the illustrated examples.

First Embodiment

A photoacoustic apparatus according to the present embodiment will be described below with reference to FIG. 1. FIG. 1 is a view schematically illustrating the photoacoustic apparatus according to the present embodiment.

The photoacoustic apparatus according to the present embodiment includes a light source 110, an optical system 120, a transducer array 130, an acoustic matching material 140, a computer 150 as a control unit and a processing unit, a display unit 160, an input unit 170, a shape acquisition unit 180, and a moving unit 190. Note that the transducer array 130 includes a function as an acoustic wave transmission unit to transmit an acoustic wave to a subject 100. Also, the transducer array 130 includes a function as an acoustic wave reception unit to receive an acoustic wave.

Figure 2:
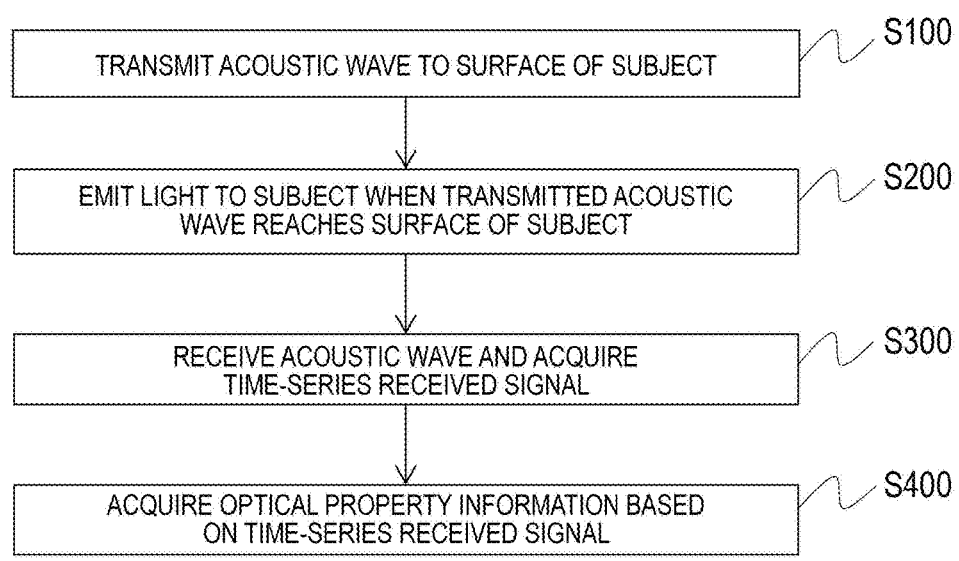
FIG. 2 is a flowchart illustrating an operation flow of the photoacoustic apparatus according to the first embodiment.

Next, an operation of the photoacoustic apparatus according to the present embodiment will be described with reference to FIG. 2. Note that the computer 150 controls an operation of each configuration of the photoacoustic apparatus.

(S100: Process for Transmitting Acoustic Wave to Surface of Subject)

The transducer array 130 transmits, to a surface 105 of the subject 100, an acoustic wave 102a as a transmission acoustic wave in such a manner that amplitude of a photoacoustic wave 104b generated on the surface 105 of the subject 100 in a next process (S200) is reduced. In the present embodiment, the computer 150 controls a waveform of the acoustic wave transmitted from the transducer array 130 in such a manner that a waveform of the acoustic wave 102a of when the acoustic wave 102a reaches the surface 105 of the subject 100 becomes antiphase of the photoacoustic wave 104b.

A part of the acoustic wave 102a is reflected by the surface 105 of the subject 100 and becomes a component of an echo 102d and a part of the acoustic wave 102a is transmitted and becomes a component of an acoustic wave 102b. The acoustic wave 102b is reflected by an optical absorber 101 as a reflector and an echo 102c is generated.

<Determination Method of Transmission Waveform>

In the following, an example of a method for determining a waveform, which is to be transmitted from the transducer array 130 in order to reproduce an antiphase waveform of the photoacoustic wave 104b, will be described. Note that a method is not limited to the following method as long as an antiphase waveform of the photoacoustic wave 104b can be reproduced.

First, the computer 150 estimates a waveform of the photoacoustic wave 104b based on a size or a shape of the surface 105 (source of reflected wave) of the subject 100. In the photoacoustic wave, a waveform having a different frequency characteristic is generated depending on a shape of a substance. As a general solution, it is known that when a shape of the optical absorber is a slab shape, the waveform becomes a waveform protruded upward, and in a case of a spherical shape, the waveform becomes an N-shaped waveform. Thus, from a shape of the source of a reflected wave, a waveform of the photoacoustic wave generated in the source of a reflected wave can be estimated.

Subsequently, after performing discrete Fourier transform on an estimated waveform the photoacoustic wave 104b and separating the waveform into each frequency, the computer 150 applies a phase of 180 degrees to each frequency term. Thus, an antiphase waveform of the photoacoustic wave 104b can be acquired.

Then, the computer 150 can calculate, by a photoacoustic wave equation, a waveform to be transmitted from the transducer array 130 in order to reproduce the estimated antiphase waveform of the photoacoustic wave 104b. Note that according to a waveform to be reproduced, the computer 150 can arbitrarily calculate a waveform to be transmitted by the photoacoustic wave equation.

Also, the computer 150 can select, as a transmission waveform, transmission waveform data corresponding to antiphase of the photoacoustic wave 104b generated on the surface 105 of the subject 100 from a plurality of pieces of transmission waveform data housed in a storage unit 151 in the computer 150. Here, the computer 150 can select the transmission waveform data based on shape information of the surface 105 of the subject 100, which information is acquired by the shape acquisition unit 180.

<Amplitude of Transmission Waveform>

Incidentally, when amplitude of the transmission waveform is small, amplitude of the acoustic wave 102b at generation may become smaller than amplitude of the photoacoustic wave 104b generated in the next process (S200) and there is not much effect to reduce amplitude of a reflected wave 104c. On the other hand, when amplitude of the transmission waveform is increased, amplitude of the acoustic wave 102b may become larger than that of the photoacoustic wave 104b and amplitude of the echo 102c of the acoustic wave 102b becomes large. In these cases, a virtual image based on the reflected wave 104b or the echo 102c may appear in optical property information acquired in a later process (S400).

Thus, the computer 150 preferably determines amplitude of the transmission waveform in such a manner that a difference between amplitude of the photoacoustic wave 104b and amplitude of the acoustic wave 102b becomes small. Moreover, the computer 150 preferably determines amplitude of the transmission waveform in such a manner that amplitude of the photoacoustic wave 104b and amplitude of the acoustic wave 102a at the generation become identical.

Also, the computer 150 preferably determines amplitude of the transmission waveform in consideration of influence of attenuation in the subject. Note that attenuation of an acoustic wave varies depending on a frequency, and thus, correction is preferably performed with different values respectively on frequencies of the transmission waveform.

Also, based on a light quantity value in a reflection source and a typical absorption coefficient, the computer 150 can estimate amplitude (initial sound pressure) of the photoacoustic wave generated in the reflection source and can control amplitude of the transmission waveform in such a manner that amplitude of the acoustic wave 102b becomes estimated amplitude of the photoacoustic wave.

Also, a user may be able to set amplitude of the transmission waveform with the input unit 170. Accordingly, the user can arbitrarily set amplitude of the transmission waveform with which a virtual image is reduced, while checking optical property information displayed on the display unit 160.

<Transmission Method of Acoustic Wave>

The transducer array 130 can transmit the transmission waveform determined in such a manner by the following method.

The transducer array 130 can form the acoustic wave 102b by forming a great number of virtual point sound sources along a shape of a source of a reflected wave by using a known method such as an acoustic radiation force impulse (ARFI) described in "Acoustic radiation force impulse imaging of myocardial radio-frequency ablation: initial in vivo results", Fahey et al., IEEE Transactions on Ultrasonics, Ferroelectrics and Frequency Control, Volume 52, Issue 4, April 2005 Page(s): 631-641. Here, based on shape information acquired by the shape acquisition unit 180, the computer 150 can determine positions to form the virtual point sound sources. The computer 150 can control a transmission waveform of the transducer array 130 in such a manner that the virtual point sound sources can be formed in determined positions.

In the present embodiment, the transducer array 130 determines a transmission waveform in such a manner that a waveform of the acoustic wave 102b becomes antiphase of the photoacoustic wave 104b and reduces amplitude of the photoacoustic wave 104b. However, a method is not limited to this method as long as amplitude of the photoacoustic wave generated in the source of a reflected wave can be reduced. That is, the transmission waveform is not limited to antiphase of the photoacoustic wave generated in the source of a reflected wav and only needs to be a waveform with which amplitude of the photoacoustic wave generated in the source of a reflected wave is reduced.

(S200: Process for Emitting Light to Subject when Transmitted Acoustic Wave Reaches Surface of Subject)

At an estimated time point at which the acoustic wave 102a transmitted in S100 reaches the surface 105 of the subject 100, the light source 110 generates pulsed light 121 and the pulsed light 121 is emitted to the subject 100 through the optical system 120. Here, the emitted pulsed light 121 is absorbed by the optical absorber 101 and the optical absorber 101 expands instantaneously, and thus, a photoacoustic wave 103 is generated.

On the other hand, the pulsed light 121 is also absorbed on the surface 105 of the subject 100 and a photoacoustic wave is generated. The photoacoustic wave generated on the surface 105 of the subject 100 is classified broadly into a photoacoustic wave 104a generated in a direction of the transducer array 130 and a photoacoustic wave 104b generated in an opposite direction of the transducer array 130. The photoacoustic wave 104a is propagated in the acoustic matching material 140 and reaches the transducer array 130. The photoacoustic wave 104b is propagated in the subject 100 and is reflected by the optical absorber 101, and thus, a reflected wave 104c is generated.

Figure 3:
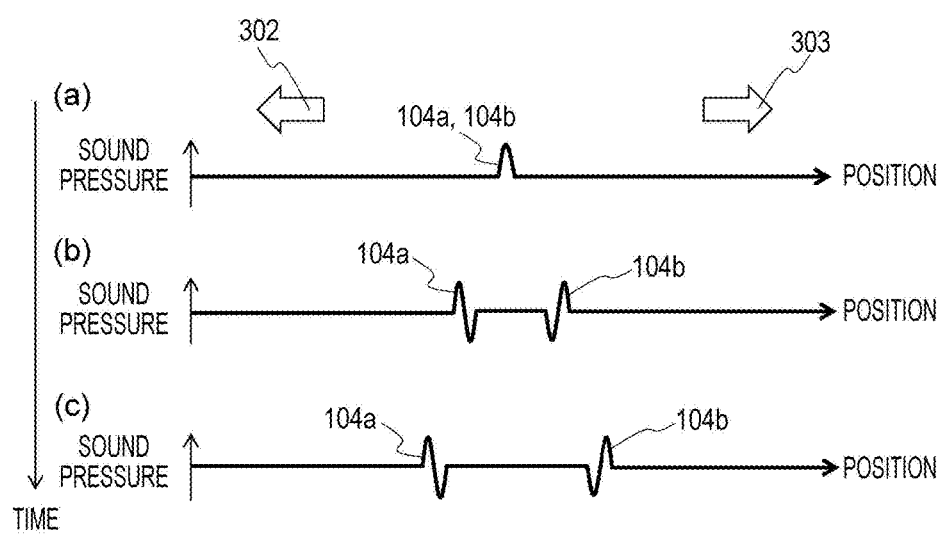
FIG. 3 is a view illustrating time progress of an acoustic wave.

FIG. 3 is a view illustrating, as a comparison example, progress of a waveform of a photoacoustic wave generated on the surface 105 of the subject 100. The photoacoustic wave generated on the surface 105 of the subject 100 spreads isotropically. Thus, the photoacoustic wave progresses over time in a direction 302 of the transducer array 130 and in an opposite direction 303 of the transducer array 130.

Figure 4:
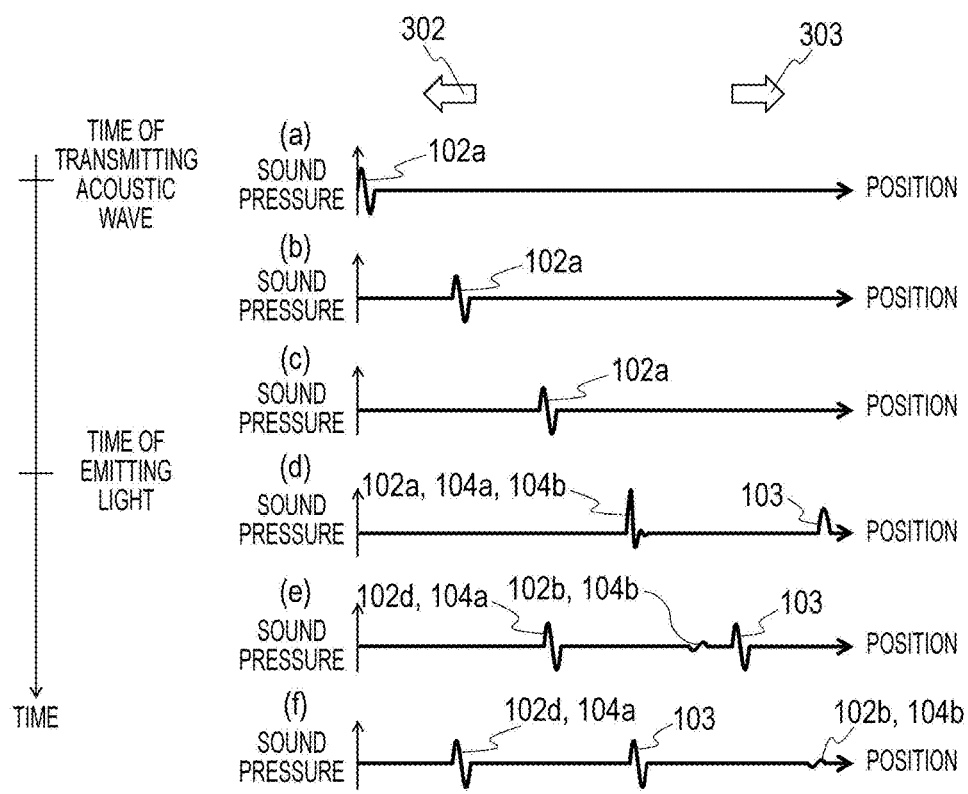
FIG. 4 is a different view illustrating time progress of the acoustic wave.

FIG. 4 is a view illustrating progress of an acoustic wave in a case where the photoacoustic waves 104a and 104b are generated when the acoustic wave 102a reaches the surface 105 of the subject 100.

First, in S100, the transducer array 130 transmits the acoustic wave 102a at a time point illustrated in (a) of FIG. 4. As time passes from (a) to (c) of FIG. 4, the acoustic wave 102a is propagated in the opposite direction 303 of the transducer array 130.

Next, in S200, the light source 110 generates the pulsed light 121 at a time point illustrated in (d) of FIG. 4 and the pulsed light 121 is emitted to the subject 100. Then, the photoacoustic waves 104a and 104b are generated on the surface 105 of the subject 100. Also, the photoacoustic wave 103 is generated in the optical absorber 101. On the other hand, the acoustic wave 102a reaches the surface 105 of the subject 100 at the time point illustrated in (d) of FIG. 4 and interferes with the photoacoustic waves 104a and 104b generated on the surface 105 of the subject 100.

Subsequently, an interference wave between the photoacoustic wave 104a and the echo 102d and the photoacoustic wave 103 progress in the direction 302 of the transducer array 130. On the other hand, an interference wave between the acoustic wave 102b and the photoacoustic wave 104b progresses in the opposite direction 303 of the transducer array 130. Note that in the present embodiment, description will be made on the assumption of a case where the echo 102d is small compared to the photoacoustic wave 104a and can be ignored.

At time points illustrated in (e) and (f) of FIG. 4, it can be understood that the acoustic wave 102b interferes with the photoacoustic wave 104b and amplitude of the photoacoustic wave 104b is reduced. That is, amplitude of the interference wave between the acoustic wave 102b and the photoacoustic wave 104b becomes smaller than amplitude of the photoacoustic wave 104b illustrated in (b) and (c) of FIG. 3. Thus, amplitude of a reflected wave of the interference wave between the acoustic wave 102b and the photoacoustic wave 104b also becomes smaller than amplitude of the reflected wave of the photoacoustic wave 104b.

On the other hand, the photoacoustic wave 103 generated in the optical absorber 101 does not form an interference wave with a different acoustic wave which interference wave progresses in the direction 302 of the transducer array 130. That is, decrease in amplitude of the photoacoustic wave 103 due to interference with a different acoustic wave is not caused much. Thus, the photoacoustic wave 103 reaches the transducer array 130 while amplitude thereof is maintained substantially.

<Light Emission Time Point>

The computer 150 controls the light source 110 to generate pulsed light at an estimated time point at which the acoustic wave 102 transmitted in S100 reaches the surface 105 of the subject 100. The reached time point can be determined by estimating propagation time (time of flight) of the acoustic wave 102a from the transducer array 130 to the surface 105 of the subject 100. The computer 150 can estimate the propagation time from a distance between the transducer array 130 and the surface 105 of the subject 100 and an average speed of sound of the acoustic wave 102a in a propagation path. Note that any method can be employed as long as propagation time can be estimated.

Note that when the propagation time of the transmission acoustic wave is in an ignorable degree in reduction of the amplitude of the photoacoustic wave generated in the source of a reflected wave, the light source may generate light at a time point at which an acoustic wave is transmitted from a transducer.

(S300: Process for Receiving Acoustic Wave and Acquiring Time-Series Received Signal)

In the process, the transducer array 130 receives the acoustic wave generated in S100 and S200 and converts the acoustic wave into a time-series received signal S1 (t) which is an analog signal. It is assumed that t indicates time and t=0 is a time point at which the light source 110 generates the pulsed light 121. That is, the computer 150 performs control to start acquiring a received signal at a time point at which the light source 110 generates the pulsed light 121. For example, the computer 150 can control acquisition of the received signal by controlling, for example, driving of the transducer array 130 or housing, into a memory, of a received signal output from the transducer array 130.

Also, the computer 150 performs processing of amplification and A/D conversion on the time-series received signal output from the transducer array 130 and houses the processed signal into the storage unit 151. Note that the time-series received signal is a concept including both of an analog signal output from the transducer array 130 and a digital signal after the A/D conversion.

Figure 5:
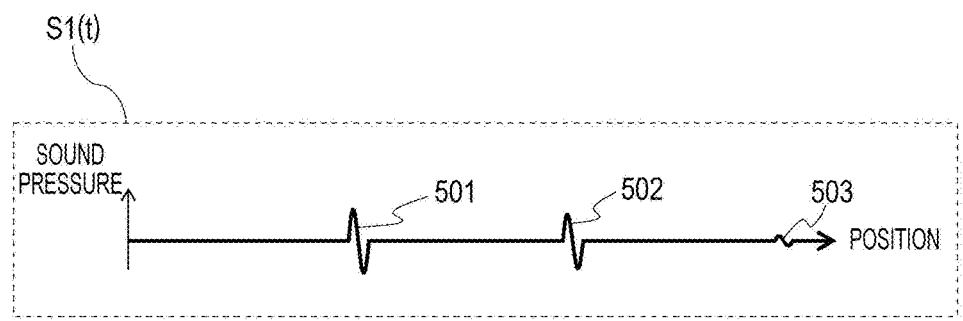
FIG. 5 is a view illustrating a time-series photoacoustic signal.

FIG. 5 is a view illustrating the time-series received signal S1 (t) acquired in the present process. First, the transducer array 130 receives the interference wave between the photoacoustic wave 104a and the echo 102d propagated in the direction of the transducer array 130 and acquires a received signal 501. Subsequently, the transducer array 130 receives the photoacoustic wave 103 generated in the optical absorber 101 and acquires a received signal 502. Then, the transducer array 130 receives a reflected wave (interference wave between reflected wave 104c and echo 102c) of the interference wave between the photoacoustic wave 104b and the acoustic wave 102b and acquires a received signal 503. In S100, since amplitude of the interference wave between the acoustic wave 102b and the photoacoustic wave 104b is a transmission waveform which becomes smaller than amplitude of the photoacoustic wave 104b, amplitude of the received signal 503 is small. On the other hand, since the photoacoustic wave 103 generated in the optical absorber 101 reaches the transducer array 130 while amplitude thereof is substantially maintained, amplitude of the received signal 502 is substantially the same with the amplitude of the photoacoustic wave 103 at generation.

Note that when amplitude of the echo 102d is large compared to the amplitude of the photoacoustic wave 104a and cannot be ignored, the amplitude of the photoacoustic wave 104a is not maintained due to interference with the echo 102d. Thus, the computer 150 may estimate the amplitude of the echo 102d and may restore the amplitude of the photoacoustic wave 104a based on the estimated amplitude of the echo 102d.

<Arrangement of Transducer Array>

In the present embodiment, an acoustic wave transmission unit to transmit an acoustic wave and an acoustic wave reception unit to receive an acoustic wave is a single transducer array 130 and the both are arranged on one side of the surface 105 (source of reflected wave) of the subject 100. Thus, between the photoacoustic wave 104a and the photoacoustic wave 104b generated on the surface 105 of the subject 100, amplitude of the photoacoustic wave 104b generated in the opposite direction of the transducer array 130 can be selectively reduced. However, according to the present invention, arrangements of the acoustic wave transmission unit and the acoustic wave reception unit can be determined according to a direction of generation (direction of propagation) of a photoacoustic wave amplitude of which is to be reduced among the photoacoustic waves generated in the source of a reflected wave.

For example, a user sets, with the input unit 170, a specific area and a specific direction in which amplitude of a photoacoustic wave is to be reduced. Subsequently, based on the set specific area and specific direction, the computer 150 determines a position of the transducer array 130 during transmission of an acoustic wave and a position of the transducer array 130 during reception of an acoustic wave. Then, the moving unit 190 can move the transducer array 130 to a position of the transducer array 130 determined by the computer 150.

(S400: Process for Acquiring Optical Property Information Based on Time-Series Received Signal)

Based on the time-series received signal S1 (t) acquired in S300, the computer 150 acquires optical property information of the subject 100. The computer 150 acquires the optical property information based on the time-series received signal S1 (t) including the received signal 503 of the reflected wave amplitude of which is smaller than that of the reflected wave 104c of the photoacoustic wave 104b. Also, the computer 150 acquires the optical property information based on the time-series received signal S1 (t) in which amplitude of the photoacoustic wave 103 at generation is substantially maintained. Thus, in the present embodiment, optical property information in which decrease of quantitativity due to the reflected wave 104c of the photoacoustic wave 104b is controlled can be acquired.

For example, computer 150 can acquire, from the time-series received signal S1 (t), initial sound pressure distribution of the photoacoustic wave as the optical property information by publicly-known image reconstruction. Also, by acquiring light quantity distribution, in the subject 100, of the light emitted to the subject 100 in S200 and correcting the initial sound pressure distribution with the light quantity distribution, the computer 150 can acquire absorption coefficient distribution as the optical property information. Moreover, the computer 150 can acquire, by using light of a plurality of wavelengths, absorption coefficient distribution corresponding to each of the wavelengths. By using the absorption coefficient distribution, the computer 150 can acquire, as the optical property information, a concentration of a substance included in the subject 100.

In the following, each configuration of the photoacoustic apparatus according to the present embodiment will be described.

(Subject 100 and Optical Absorber 101)

These are not what configures a part of the photoacoustic apparatus of the present invention but will be described in the following. The photoacoustic apparatus of the present invention has been made mainly for a diagnosis of a malignant tumor, a blood vessel disease, or the like of a human or an animal, a follow-up of a chemical treatment, or the like. Thus, as a subject, a living body, specifically an object region of diagnosis, such as a breast, a neck, or a stomach of a human body or an animal is assumed.

Also, an optical absorber inside the subject is what having a relatively high absorption coefficient inside the subject. For example, when a human body is a measurement object, a malignant tumor, which includes a great amount of oxyhemoglobin, deoxyhemoglobin, or methemoglobin or a great number of blood vessels or new blood vessels including a great amount thereof, becomes an object of the optical absorber. In addition, a plaque on a carotid artery wall or the like also becomes the object.

(Light Source 110)

A light source is preferably a pulsed light source which can generate pulsed light of an order of a several nano seconds to a several micro seconds. Specifically, in order to generate a photoacoustic wave effectively, a pulse width around ten nano seconds is used. As the light source, a light emitting diode or the like can be used instead of a laser. As the laser, various lasers such as a solid-state laser, a gas laser, a dye laser, and a semiconductor laser can be used. A wavelength of a light source to be used is preferably a wavelength with which light is propagated inside the subject. Specifically, when the subject is a living body, the wavelength is 500 nm to 1200 nm.

(Optical System 120)

The optical system 120 is a member to lead, to the subject 100, light emitted from a light source while making the light into an intended light distribution shape. The optical system 120 includes an optical part such as a lens or a mirror, an optical waveguide such as an optical fiber, and the like. For example, an optical part is a mirror to reflect light, a lens to collect and increase light and to change a shape thereof, a diffuser panel to diffuse light, or the like. Any kind of optical system 120 can be used as long as the light emitted from the light source is emitted to a subject in an intended shape. Note that it is preferable that light is expanded to an area of a certain degree instead of being collected by a lens in terms of safety to a living body and of a wider diagnosis area. Also, to make it easier to transmit an acoustic wave to an area to which light is emitted, the optical system 120 is configured in such a manner as to light directly below the transducer array 130.

(Transducer Array 130)

As a transducer used for the transducer array 130, any transducer such as what uses a piezoelectric phenomenon, optical resonance, a change in capacitance, or the like can be used as long as an acoustic wave can be transmitted/received.

Note that by including a transmission/reception function of an acoustic wave like the present embodiment, the transducer array 130 can easily receive an acoustic wave in the same area and can easily conserve space, for example. However, functions of the acoustic wave transmission unit and the photoacoustic wave reception unit may be respectively included in different transducer arrays.

(Acoustic Matching Material 140)

The acoustic matching material 140 is not what configures a part of the photoacoustic apparatus of the present invention but will be described below. The acoustic matching material 140 is a material provided between the subject 100 and the transducer array 130 to perform acoustic matching of the subject 100 and the transducer array 130. As the acoustic matching material 140, for example, a gel including water, oil, alcohol, or the like is used.

(Computer 150)

As the computer 150, a typical workstation or the like is used. Correction processing, image reconstruction processing, or the like is performed by software programmed in advance. Note that in the present embodiment, various kinds of processing executed by the computer 150 may be different apparatuses.

Also, instead of the software processing performed in a workstation, a property such as acoustic impedance of a subject, or optical property information can be acquired by hardware processing.

A calculation unit 152 in the computer 150 can perform predetermined processing on an electric signal output from the transducer array 130.

Also, the calculation unit 152 can control an operation of each configuration of the photoacoustic apparatus. For example, the calculation unit 152 can control time point for emitting pulsed light generated in the light source and can control time point for transmitting/receiving an electric signal with the pulsed light as a trigger signal. By controlling a transmission wave of each transducer in the transducer array 130, the calculation unit 152 can arbitrarily control a wave front of the acoustic wave transmitted by the transducer array 130.

That is, the calculation unit 152 can include a plurality of functions such as a signal processing unit, a control unit, and the like.

The calculation unit 152 typically includes an element such as a CPU, a GPU, or an A/D converter or a circuit such as an FPGA, or an ASIC. Note that the calculation unit 152 does not necessarily include only one element or circuit and may include a plurality of elements or circuits. Also, processing performed by the calculation unit 152 may be executed by any element or circuit.

Also, the storage unit 151 in the computer 150 typically includes a storage medium such as a ROM, a RAM, or a hard disk. Note that the storage unit 151 does not necessarily include only one storage medium and may include a plurality of storage media.

Also, it is preferable that the computer 150 can perform pipeline processing of a plurality of signals simultaneously. Accordingly, a period of time before the optical property information is acquired can be reduced.

Note that processing performed by the computer 150 can be stored in the storage unit 151 as a program to be executed by the calculation unit 152. The storage unit 151 into which the program is stored is a non-transitory storage medium.

(Display Unit 160)

The display unit 160 is an apparatus to display optical property information output from a signal processing apparatus. Typically, a liquid crystal display or the like is used but a display of a different type such as a plasma display, an organic electroluminescence display, or an FED may also be used. Note that the display unit 160 may be provided separately from the photoacoustic apparatus of the present invention.

(Input Unit 170)

The input unit 170 is a member with which a user can specify intended information in order to input the intended information into the computer 150. As the input unit 170, a keyboard, a mouse, a touch panel, a dial, a button, or the like can be used. When a touch panel is employed as the input unit 170, the display unit 160 may double as the input unit 170.

(Shape Acquisition Unit 180)

The shape acquisition unit 180 is a member which can acquire outer shape information or inner shape information of a substance. As the shape acquisition unit 180, an optical camera to acquire outer shape information, a transducer array to acquire a B mode image, or the like can be employed. Note that when the shape acquisition unit 180 is a member to acquire shape information by a B mode image, the transducer array 130 may be used as the shape acquisition unit 180.

(Moving Unit 190)

The moving unit 190 is an apparatus to move the transducer array 130 to a set position at a time point set by the computer 150. The moving unit 190 may move the transducer array 130 in a step-and-repeat manner or in a continuous manner. Also, the moving unit 190 may change velocity of movement during the movement.

Second Embodiment

In the second embodiment, a received signal of a photoacoustic wave generated in a source of a reflected wave is extracted from a time-series received signal acquired by not transmitting an acoustic wave and receiving only a photoacoustic wave. Then, the second embodiment is different from the first embodiment in a point that a transmission waveform to reduce the photoacoustic wave generated in the source of a reflected wave is determined based on the extracted received signal of the photoacoustic wave generated in the source of a reflected wave. In the present embodiment, description will be also made with reference to the photoacoustic apparatus illustrated in FIG. 1. Description of a configuration which is the same with that of the first embodiment will not be repeated.

Figure 6:
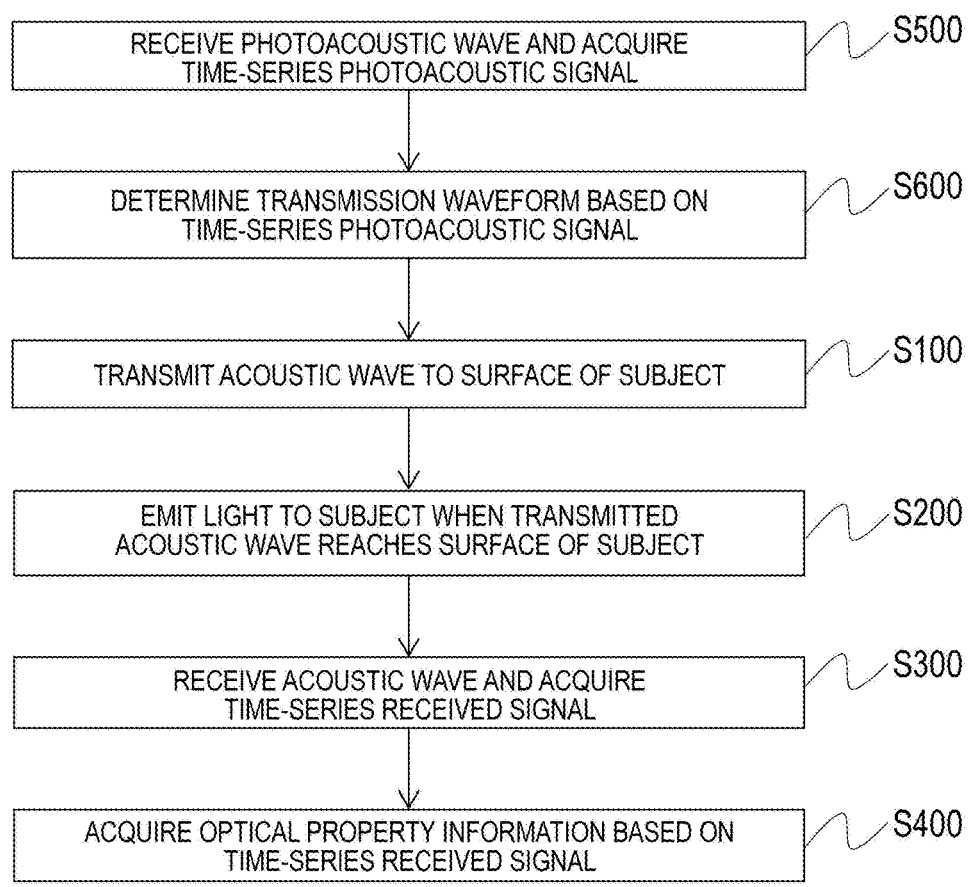
FIG. 6 is a flowchart illustrating an operation flow of a photoacoustic apparatus according to a second embodiment.

In the following, an operation of a photoacoustic apparatus according to the present embodiment will be described with reference to a flowchart illustrated in FIG. 6.

(S500: Process for Receiving Photoacoustic Wave and Acquiring Time-Series Photoacoustic Signal)

In the process, pulsed light 121 emitted from a light source 110 as auxiliary light is emitted to a subject 100 through an optical system 120. Then, on a surface 105 of the subject 100, photoacoustic waves 104a and 104b are generated. Also, in an optical absorber 101 in the subject 100, a photoacoustic wave 103 is generated. Subsequently, a transducer array 130 receives a photoacoustic wave including the photoacoustic waves 103 and 104a and a reflected wave 104c of the photoacoustic wave 104b and converts the photoacoustic wave into a time-series received signal S2 (t) (not illustrated). Also, the computer 150 performs processing of amplification and A/D conversion on the time-series received signal S2 (t) output from the transducer array 130 and houses the processed signal into a storage unit 151. Note that in the present process, a time-series received signal acquired by receiving a photoacoustic wave will be referred to as a time-series photoacoustic signal.

(S600: Process for Determining Transmission Waveform Based on Time-Series Photoacoustic Signal)

The computer 150 determines a transmission waveform of an acoustic wave 102b to be transmitted in a next process (S100) based on the time-series photoacoustic signal S2 (t) acquired in S500.

For example, the computer 150 extracts, from the time-series photoacoustic signal S2 (t), a received signal of the photoacoustic wave 104a generated on the surface 105 of the subject 100 and estimates a waveform of the photoacoustic wave 104a at generation. Subsequently, the computer 150 determines, from the estimated waveform of the photoacoustic wave 104a, a transmission waveform to reduce amplitude of the photoacoustic wave 104b. Since the photoacoustic wave is generated isotropically, the photoacoustic wave 104a and the photoacoustic wave 104b include similar waveforms. Thus, it can be considered that a waveform of the photoacoustic wave 104a is a waveform of the photoacoustic wave 104b. As a method to determine, from a waveform of the photoacoustic wave 104a, a transmission waveform to reduce the photoacoustic wave 104b, a method described in S100 can be employed.

Note that by a method described in the following, a received signal of the photoacoustic wave 104a can be extracted from the time-series photoacoustic signal S2 (t) acquired in S500. However, a method is not limited to the following method as long as a received signal of the photoacoustic wave 104a can be extracted.

Since the surface 105 of the subject 100 is a part to which light is directly emitted, amplitude of the photoacoustic wave 104a becomes relatively large. Thus, the computer 150 can extract, from the time-series photoacoustic signal S2 (t), a waveform having the largest amplitude as a received signal of the photoacoustic wave 104a.

Also, since the surface 105 of the subject 100 is close to the transducer array 130, the photoacoustic wave 104a reaches the transducer array 130 prior to the other photoacoustic waves. Thus, the computer 150 can extract, as a received signal of the photoacoustic wave 104a, a waveform which has amplitude equal to or larger than a threshold and is output from the time-series photoacoustic signal S2 (t) in the beginning.

Also, the time-series photoacoustic signal S2 (t) may be displayed on the display unit 160 and an arbitrary waveform may be selected, as a received signal of the photoacoustic wave 104a, with the input unit 170 by a user.

Also, the initial sound pressure distribution acquired from the time-series photoacoustic signal S2 (t) may be displayed on the display unit 160 and a user may specify an arbitrary position on the initial sound pressure distribution with the input unit 170, and thus, a received signal of the photoacoustic wave 104a may be extracted. For example, a plurality of photoacoustic signals, which is used to reconstruct an initial sound pressure at a specified position, can be averaged and selected as a received signal of the photoacoustic wave 104a. Also, among the plurality of photoacoustic signals, which is used to reconstruct an initial sound pressure at a specified position, a waveform of an arbitrary photoacoustic signal can be selected as a received signal of the photoacoustic wave 104a. Note that it is preferable that a photoacoustic signal output from a transducer which anticipates a specified position in a direction of high directionality is selected as a received signal of the photoacoustic wave 104a.

Subsequently, in S100, the transducer array 130 transmits the acoustic wave 102a in a transmission waveform determined in S600. Then, similarly to the first embodiment, processes of S200 to S400 are executed.

As described, in the present embodiment, a transmission waveform is determined based on a received signal of an actually generated photoacoustic wave. Thus, compared to an embodiment to estimate a waveform of a generated photoacoustic wave and to determine a transmission waveform, a transmission waveform to reduce amplitude of a photoacoustic wave can be determined accurately.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-209625, filed 2013 Oct. 4, which is hereby incorporated by reference herein in its entirety.

What is claimed is:

1. A photoacoustic apparatus comprising:
    an acoustic wave transmission unit configured to transmit a transmission acoustic wave to a specific area;
    a control unit configured to control a transmission waveform of the transmission acoustic wave transmitted from the acoustic wave transmission unit;
    a light source configured to generate light emitted to an area including the specific area when the acoustic wave reaches the specific area;
    an acoustic wave reception unit configured to receive the acoustic wave and to output a time-series received signal; and
    a signal processing unit configured to acquire optical property information based on the time-series received signal,
    wherein the control unit controls the transmission waveform in such a manner that amplitude of a photoacoustic wave generated in the specific area is reduced by the transmission acoustic wave transmitted from the acoustic wave transmission unit.

2. The photoacoustic apparatus according to claim 1, wherein the control unit controls the transmission waveform in such a manner that a waveform of the transmission acoustic wave in the specific area becomes antiphase of a waveform of the photoacoustic wave generated in the specific area.

3. The photoacoustic apparatus according to claim 1, wherein the control unit determines the transmission waveform based on the time-series received signal.

4. The photoacoustic apparatus according to claim 3, wherein the control unit extracts, from the time-series received signal, a received signal of the photoacoustic wave generated in the specific area and determines the transmission waveform based on the received signal of the photoacoustic wave generated in the specific area.

5. The photoacoustic apparatus according to claim 4, wherein the control unit determines the transmission waveform by a photoacoustic wave equation based on the received signal of the photoacoustic wave generated in the specific area.

6. The photoacoustic apparatus according to claim 4, further comprising a storage unit which houses a plurality of pieces of transmission waveform data,
    wherein the control unit selects the transmission waveform from the plurality of pieces of transmission waveform data based on the received signal of the photoacoustic wave generated in the specific area.

7. The photoacoustic apparatus according to claim 1, wherein the control unit estimates a waveform of the photoacoustic wave generated in the specific area and determines the transmission waveform based on the estimated waveform of the photoacoustic wave.

8. The photoacoustic apparatus according to claim 7, further comprising a shape acquisition unit configured to acquire shape information of the specific area,
    wherein the control unit estimates, based on the shape information, a waveform of the photoacoustic wave generated in the specific area.

9. The photoacoustic apparatus according to claim 7, wherein the control unit determines the transmission waveform by a photoacoustic wave equation based on the estimated waveform.

10. The photoacoustic apparatus according to claim 7, further comprising a storage unit which houses a plurality of pieces of transmission waveform data,
    wherein the control unit selects the transmission waveform from the plurality of pieces of transmission waveform data based on the estimated waveform.

11. The photoacoustic apparatus according to claim 1, wherein the acoustic wave transmission unit and the acoustic wave reception unit are arranged on one side of the specific area.

12. The photoacoustic apparatus according to claim 1, wherein the acoustic wave transmission unit and the acoustic wave reception unit include a single transducer array.

13. The photoacoustic apparatus according to claim 1, further comprising a moving unit configured to move the acoustic wave transmission unit and the acoustic wave reception unit in such a manner that amplitude of a photoacoustic wave generated in a specific direction in the specific area is reduced.

14. The photoacoustic apparatus according to claim 1, wherein the control unit controls the transmission waveform in such a manner that amplitude of a photoacoustic wave generated in a specific direction in the specific area is reduced by the transmission acoustic wave transmitted from the acoustic wave transmission unit.

15. An operation method of a photoacoustic apparatus, comprising:
    transmitting a transmission acoustic wave to a specific area;
    emitting light to an area including the specific area when the transmission acoustic wave reaches the specific area;
    receiving the acoustic wave and acquiring a time-series received signal; and
    acquiring optical property information based on the time-series received signal,
    wherein in transmitting the transmission acoustic wave to the specific area, the transmission acoustic wave having a transmission waveform to reduce amplitude of a photoacoustic wave generated in the specific area is transmitted.

16. An operation method of the photoacoustic apparatus according to claim 15, comprising:
   emitting auxiliary light to an area including the specific area before transmitting the transmission acoustic wave to the specific area;
   receiving a photoacoustic wave generated by the emission of the auxiliary light and acquiring a time-series photoacoustic signal; and
   determining, based on the time-series photoacoustic signal, a transmission waveform of the transmission acoustic wave transmitted to the specific area.

17. A non-transitory computer-readable storage medium storing a program for causing a computer to execute an operation method of the photoacoustic apparatus according to claim 15.

18. A photoacoustic apparatus comprising:
   an acoustic wave transmission unit configured to transmit a transmission acoustic wave to a specific area;
   a light source configured to generate light emitted to an area including the specific area when the acoustic wave reaches the specific area;
   an acoustic wave reception unit configured to receive the acoustic wave and to output a time-series received signal; and
   a signal processing unit configured to acquire optical property information based on the time-series received signal,
   wherein the acoustic wave transmission unit transmits the transmission acoustic wave which becomes antiphase of a waveform of a photoacoustic wave generated in the specific area.

\* \* \* \* \*